(12) United States Patent
Young et al.

(10) Patent No.: US 11,974,878 B2
(45) Date of Patent: *May 7, 2024

(54) ULTRASONIC COUPLING DEVICE

(71) Applicant: 3M INNOVATIVE PROPERTIES COMPANY, St. Paul, MN (US)

(72) Inventors: Alexi J. Young, Shoreview, MN (US); Ronald D. Jesme, Plymouth, MN (US); Nicholas T. Gabriel, Grand Rapids, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 168 days.

This patent is subject to a terminal disclaimer.

(21) Appl. No.: 17/610,672

(22) PCT Filed: Jun. 25, 2020

(86) PCT No.: PCT/IB2020/056035
§ 371 (c)(1),
(2) Date: Nov. 11, 2021

(87) PCT Pub. No.: WO2020/261182
PCT Pub. Date: Dec. 30, 2020

(65) Prior Publication Data
US 2022/0211344 A1    Jul. 7, 2022

Related U.S. Application Data

(60) Provisional application No. 62/866,403, filed on Jun. 25, 2019.

(51) Int. Cl.
*A61N 7/00*     (2006.01)
*A61B 8/00*     (2006.01)
(Continued)

(52) U.S. Cl.
CPC .............. *A61B 8/4281* (2013.01); *A61N 7/00* (2013.01); *B32B 3/08* (2013.01); *B32B 3/266* (2013.01);
(Continued)

(58) Field of Classification Search
CPC ... A61B 8/4281; A61B 8/4236; A61B 8/4472; A61B 8/44; A61B 8/4272; A61B 8/4444;
(Continued)

(56) References Cited

U.S. PATENT DOCUMENTS 5,078,149 A    1/1992    Katsumata
6,048,323 A    4/2000    Hon
(Continued)

FOREIGN PATENT DOCUMENTS

CN    105056257       11/2015
CN    109187075 A      6/2018
(Continued)

OTHER PUBLICATIONS

Drtina, "Highly Cross-Linked Azlactone Functional Supports of Tailorable Polarity", Macromolecules, 1996, vol. 29, No. 13, pp. 4486-4489.
(Continued)

*Primary Examiner* — Daniel Pihulic

(57) ABSTRACT

An ultrasonic coupling device. The ultrasonic coupling device includes a hydrogel wherein the hydrogel has a water content of at least 10 wt %; and a near field communication device.

19 Claims, 1 Drawing Sheet

(51) Int. Cl.
  *B32B 3/08* (2006.01)
  *B32B 3/26* (2006.01)
  *B32B 7/12* (2006.01)
  *B32B 27/08* (2006.01)
  *B32B 27/30* (2006.01)

(52) U.S. Cl.
  CPC ............... *B32B 7/12* (2013.01); *B32B 27/08* (2013.01); *B32B 27/308* (2013.01); *B32B 2266/122* (2016.11); *B32B 2307/728* (2013.01); *B32B 2457/00* (2013.01); *B32B 2535/00* (2013.01)

(58) Field of Classification Search
  CPC .... A61B 8/56; A61N 7/00; B32B 3/08; B32B 3/266; B32B 7/12; B32B 27/08; B32B 27/308; B32B 2266/122; B32B 2307/728; B32B 2457/00; B32B 2535/00; B32B 2250/02; B32B 2250/03; B32B 9/00; B32B 27/32; B32B 27/36; B32B 27/40; A61K 49/221; A61K 49/226
  See application file for complete search history.

(56) References Cited

U.S. PATENT DOCUMENTS

| | | |
|---|---|---|
| 6,843,771 B2 | 1/2005 | Lo |
| 7,070,565 B2 | 7/2006 | Vaezy |
| 2003/0149359 A1 | 8/2003 | Smith |
| 2004/0234453 A1 | 11/2004 | Smith |
| 2006/0058705 A1 | 3/2006 | Leonetti et al. |
| 2011/0313293 A1 | 12/2011 | Lindekugel |
| 2013/0144193 A1 | 6/2013 | Lewis, Jr. |
| 2015/0305709 A1 | 10/2015 | Tomassi et al. |
| 2016/0016338 A1 | 1/2016 | Radcliffe |
| 2016/0242736 A1 | 8/2016 | Freiburg |
| 2018/0068214 A1 | 3/2018 | Jesme et al. |
| 2022/0211344 A1* | 7/2022 | Young .................... B32B 3/266 |
| 2022/0240892 A1* | 8/2022 | Young .................... B32B 3/08 |

FOREIGN PATENT DOCUMENTS

| | | | |
|---|---|---|---|
| CN | 113950292 A * | 1/2022 | ........... A61B 8/4281 |
| CN | 114096198 A * | 2/2022 | ........... A61B 8/4236 |
| EP | 0800788 | 10/1997 | |
| EP | 3990272 A1 * | 5/2022 | ........... A61B 8/4236 |
| EP | 3990273 A1 * | 5/2022 | ........... A61B 8/4281 |
| KR | 20120118864 | 10/2012 | |
| WO | WO 2015-130841 | 9/2015 | |
| WO | WO 2016-109168 | 7/2016 | |
| WO | WO 2016-160359 | 10/2016 | |
| WO | 2016190226 A1 | 12/2016 | |
| WO | WO 2017-058698 | 4/2017 | |
| WO | WO 2018-183098 | 10/2018 | |
| WO | WO 2020-261013 | 12/2020 | |
| WO | WO-2020261013 A1 * | 12/2020 | ........... A61B 8/4236 |
| WO | WO-2020261182 A1 * | 12/2020 | ........... A61B 8/4281 |

OTHER PUBLICATIONS

Haraguchi, "Compositional Effects on Mechanical Properties of Nanocomposite Hydrogels Composed of Poly(N, N-dimethylacrylamide) and Clay", Macromolecules, 2003, vol. 36, No. 15, pp. 5732-5741.

International Search Report for PCT International Application No. PCT/IB2020/056035, dated Oct. 1, 2020, 4 pages.

* cited by examiner

ULTRASONIC COUPLING DEVICE

CROSS REFERENCE TO RELATED APPLICATIONS

This application is a national stage filing under 35 U.S.C. 371 of PCT/IB2020/056035, filed Jun. 25, 2020, which claims the benefit of Provisional Application No. 62/866,403, filed Jun. 25, 2019, the disclosure of which is incorporated by reference in its/their entirety herein.

BACKGROUND

Ultrasound has been used in the medical field for decades. Traditional larger instruments are used to image the progress of pregnancies or diagnose maladies of different tissues. Besides imaging, ultrasound has been studied for its therapeutic potential and for its ability to wirelessly power devices.

SUMMARY

Thus, in one aspect, the present disclosure provides an ultrasonic coupling device comprising a hydrogel wherein the hydrogel has a water content of at least 10 wt %; and a near field communication device.

In another aspect, the present disclosure provides a system for delivering ultrasonic radiation to a subject comprising the ultrasonic coupling device of the current disclosure and an ultrasonic transducer with a probe, wherein the probe of the ultrasonic transducer is in contact with the hydrogel Various aspects and advantages of exemplary embodiments of the present disclosure have been summarized. The above Summary is not intended to describe each illustrated embodiment or every implementation of the present disclosure. Further features and advantages are disclosed in the embodiments that follow. The Drawings and the Detailed Description that follow more particularly exemplify certain embodiments using the principles disclosed herein.

DEFINITIONS

For the following defined terms, these definitions shall be applied for the entire Specification, including the claims, unless a different definition is provided in the claims or elsewhere in the Specification based upon a specific reference to a modification of a term used in the following definitions:

The terms "about" or "approximately" with reference to a numerical value or a shape means +/−five percent of the numerical value or property or characteristic, but also expressly includes any narrow range within the +/−five percent of the numerical value or property or characteristic as well as the exact numerical value. For example, a temperature of "about" 100° C. refers to a temperature from 95° C. to 105° C., but also expressly includes any narrower range of temperature or even a single temperature within that range, including, for example, a temperature of exactly 100° C. For example, a viscosity of "about" 1 Pa-sec refers to a viscosity from 0.95 to 1.05 Pa-sec, but also expressly includes a viscosity of exactly 1 Pa-sec. Similarly, a perimeter that is "substantially square" is intended to describe a geometric shape having four lateral edges in which each lateral edge has a length which is from 95% to 105% of the length of any other lateral edge, but which also includes a geometric shape in which each lateral edge has exactly the same length.

The term "substantially" with reference to a property or characteristic means that the property or characteristic is exhibited to a greater extent than the opposite of that property or characteristic is exhibited. For example, a substrate that is "substantially" transparent refers to a substrate that transmits more radiation (e.g. visible light) than it fails to transmit (e.g. absorbs and reflects). Thus, a substrate that transmits more than 50% of the visible light incident upon its surface is substantially transparent, but a substrate that transmits 50% or less of the visible light incident upon its surface is not substantially transparent.

The terms "a", "an", and "the" include plural referents unless the content clearly dictates otherwise. Thus, for example, reference to a material containing "a compound" includes a mixture of two or more compounds.

BRIEF DESCRIPTION OF THE DRAWINGS

The disclosure may be more completely understood in consideration of the following detailed description of various embodiments of the disclosure in connection with the accompanying figures, in which.

While the above-identified drawings, which may not be drawn to scale, set forth various embodiments of the present disclosure, other embodiments are also contemplated, as noted in the Detailed Description. In all cases, this disclosure describes the presently disclosed invention by way of representation of exemplary embodiments and not by express limitations. It should be understood that numerous other modifications and embodiments can be devised by those skilled in the art, which fall within the scope and spirit of this disclosure.

DETAILED DESCRIPTION

Before any embodiments of the present disclosure are explained in detail, it is understood that the invention is not limited in its application to the details of use, construction, and the arrangement of components set forth in the following description. The invention is capable of other embodiments and of being practiced or of being carried out in various ways that will become apparent to a person of ordinary skill in the art upon reading the present disclosure. Also, it is understood that the phraseology and terminology used herein is for the purpose of description and should not be regarded as limiting. The use of "including," "comprising," or "having" and variations thereof herein is meant to encompass the items listed thereafter and equivalents thereof as well as additional items. It is understood that other embodiments may be utilized and structural or logical changes may be made without departing from the scope of the present disclosure.

As used in this Specification, the recitation of numerical ranges by endpoints includes all numbers subsumed within that range (e.g. 1 to 5 includes 1, 1.5, 2, 2.75, 3, 3.8, 4, and 5, and the like).

Unless otherwise indicated, all numbers expressing quantities or ingredients, measurement of properties and so forth used in the Specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

Figure 1A:
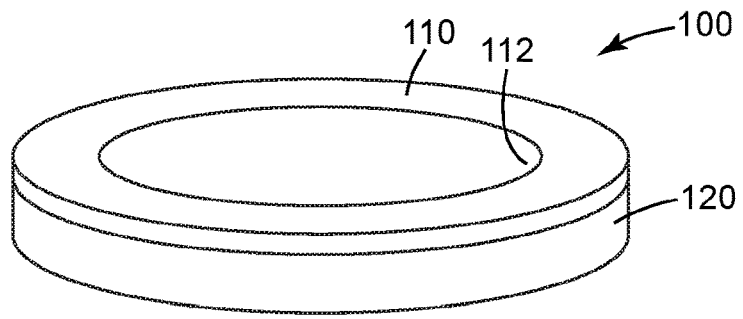
FIG. 1A is a top perspective view of one embodiment of an ultrasonic coupling device.
Figure 1B:
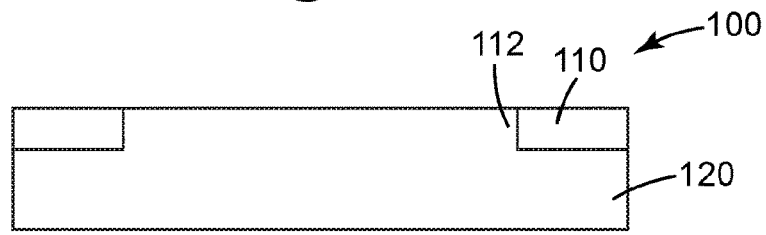
FIG. 1B is a cross sectional view of device of FIG. 1A.

An ultrasonic coupling device is provided. As illustrated in FIGS. 1A and 1B, the ultrasonic coupling device 100 includes a hydrogel 120 and a near field communication device 110 attached to the hydrogel 120. In some embodiments, the near field communication device 110 can have an aperture 112 and the hydrogel at least partially fill in the aperture 112. In some embodiments, the hydrogel can completely fill in the aperture 112.

Figure 2A:
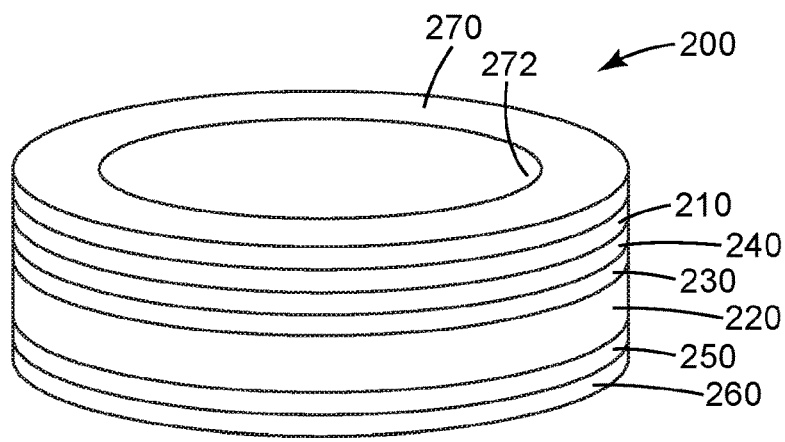
FIG. 2A is a top perspective view of an alternative embodiment of an ultrasonic coupling device.
Figure 2B:
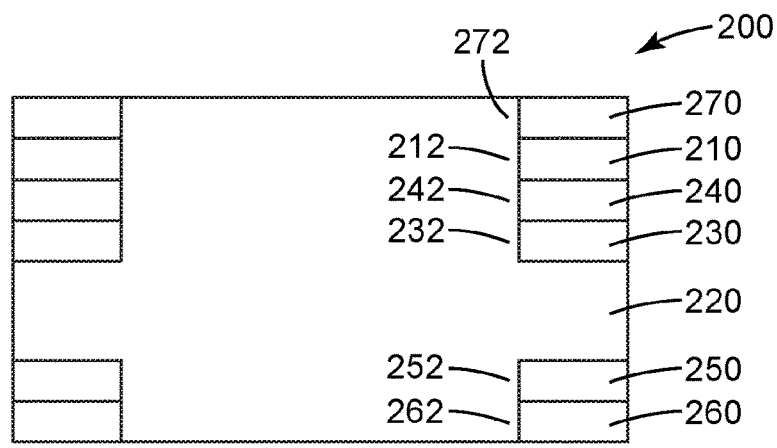
FIG. 2B is a cross sectional view of device of FIG. 2A.

In some embodiments, as illustrated in FIGS. 2A and 2B, the ultrasonic coupling device 200 can further include a polymeric substrate 230 between the hydrogel 220 and the near field communication device 210. The near field communication device 210 can have an aperture 212 and polymeric substrate 230 can have an aperture 232. The hydrogel may at least partially fill in the aperture 212 and the aperture 232. In some embodiments, the hydrogel can completely fill in the aperture 212 and the aperture 232. The ultrasonic coupling device 200 can further include an adhesive layer 240 between the near field communication device 210 and the polymeric substrate 230. The adhesive layer 240 can have an aperture 242 and the hydrogel may at least partially fill in the aperture 242. In some embodiments, the hydrogel can completely fill in the aperture 242. The ultrasonic coupling device 200 can further include a second polymeric substrate 250 on the hydrogel 220 and a second adhesive layer 260 on the second polymeric substrate 250. The second polymeric substrate 250 can have an aperture 252 and the second adhesive layer 260 can have an aperture 262. In some embodiments, the hydrogel can completely fill in the aperture 252 and the aperture 262. The hydrogel may at least partially fill in the aperture 252 and the aperture 262. The ultrasonic coupling device 200 can further include a third adhesive layer 270 on the near field communication device 210 with the near field communication device 210 in between the adhesive layer 240 and the third adhesive layer 270. The third adhesive layer 270 can have an aperture 272. The hydrogel may at least partially fill in the aperture 272. In some embodiments, the hydrogel can completely fill in the aperture 272.

In some embodiments, the hydrogel can be covalently bonded to the polymeric substrate 230 or the second polymer substrate 250. In some embodiments, the near field communication device can also include a polymeric substrate. The substrates of the present disclosure are organic polymeric substrates, more specifically a polymeric substrate comprising an abstractable atom, typically, a hydrogen atom. Exemplary polymeric substrates include polyamides such as nylons, polyesters such as polyethylene terephthalate (PET), polyolefins such as polypropylene, and polyurethanes.

Hydrogels used in the current disclosure can include those described in WO 2017/058698 A1 (Young et al.) and WO 2018/183098 A1 (Young et al.). For example, the hydrogel of the present disclosure has a water content of at least 10, 15, 20, 30, 40, or even 50 wt %. The hydrogel can be derived from an aqueous composition having a pH less than 9.5 comprising a hydrophilic monomer, a water-swellable clay, and two different water-soluble photoinitiators.

In one embodiment of the present disclosure, the hydrogel disclosed herein, after absorbing exudate or sweat or other fluids, remains attached to the polymeric substrate.

The hydrophilic monomer is a monomer that is soluble in water and/or is soluble in mixed solution comprising organic solvents miscible with water, having water as the main component. In one embodiment, the monomer has a lipophilicity index less than or equal to 20. As used herein, the term "lipophilicity index" or "LI" refers to an index for characterizing the hydrophobic or hydrophilic character of a monomer. The lipophilicity index is determined by partitioning a monomer in equal volumes (1:1) of a non-polar solvent (e.g., hexane) and a polar solvent (e.g., a 75:25 acetonitrile-water solution). The lipophilicity index is equal to the weight percent of the monomer remaining in the non-polar phase after partitioning. Monomers that are more hydrophobic tend to have a higher lipophilicity index; similarly, monomers that are more hydrophilic tend to have a lower lipophilicity index. Measurement of lipophilicity index is further described in Drtina et al., *Macromolecules*, 29, 4486-4489 (1996). Examples of non-ionic monomers that have a sufficiently low lipophilicity index include, but are not limited to, hydroxyalkyl(meth)acrylates such as 2-hydroxyethylacrylate, 3-hydroxypropylacrylate, 2-hydroxyethylmethacrylate (e.g., LI is 1), and 3-hydroxypropylmethacrylate (e.g., LI is 2); acrylamide (e.g., LI is less than 1) and methacrylamide (LI is less than 1); glycerol monomethacrylate and glycerol monoacrylate; N-alkyl (meth)acrylamides such as N-methylacrylamide (e.g., LI is less than 1), N,N-dimethylacrylamide (e.g., LI is less than 1), N-methylmethacrylamide, and N,N-dimethylmethacrylamide; N-vinylamides such as N-vinylformamide, N-vinylacetamide, and N-vinylpyrrolidone; acetoxyalky(meth) acrylates such as 2-acetoxyethylacrylate and 2-acetoxyethylmethacrylate (e.g., LI is 9); glycidyl(meth) acrylates such as glycidylacrylate and glycidylmethacrylate (e.g., LI is 11); and vinylalkylazlactones such as vinyldimethylazlactone (e.g., LI is 15).

Hydrophilic monomers are known in the art and include vinyl monomers such as (meth)acrylates and (meth)acrylamides.

Exemplary (meth)acrylate monomers include: acrylic acid (3-sulphopropyl) ester (SPA) and salts thereof, N,N-dimethylaminoethylmethacrylate and salts thereof, [2-(methacryloyloxy)ethyl]dimethyl-(3-sulfopropyl) ammonium hydroxide, [2-(methacryloyloxy)ethyl] trimethylammonium chloride, 2-hydroxyethyl(meth) acrylate, hydroxypropyl(meth)acrylate, and polyethyleneglycolmono(meth)acrylate.

Exemplary (meth)acrylamide monomers include: N-substituted (meth)acrylamide derivatives, such as N-methylacrylamide, N-ethylacrylamide, cyclopropylacrylamide, N-isopropylacrylamide, N-methylmethacrylainide, cyclopropylmethacrylamide, N-isopropylmethacrylamide, diacetone acrylamide, hydroxyethyl acrylamide, 2-acrylamido-2-methylpropane sulphonic acid (AMPS) and salts thereof; and N,N-di-substituted (meth)acrylamide derivatives, such as N,N-dimethylacrylamide, N,N-dimethylaminopropylacrylamide, N-methyl-N-ethylacrylamide, N-methyl-N-isopropylacrylamide, N-methyl-N-n-propylacrylamide, N,N-diethylacrylamide, N-acryloylpyrrolidine, N-acryloylpiperidine, N-acryloyl-N'-methylhomopiperidine, and N-acryloyl-N'-methylpiperidine, N-acryloyl morpholine or a substituted derivative thereof, and N,N dimethylaminopropylmethacrylamide.

Conventional cross-linking agents (i.e., compounds which covalently-bond polymer chains together) are suitably used to provide the necessary mechanical stability and optionally to control the adhesive properties of the hydrogel. The amount of cross-linking agent required will be readily apparent to those skilled in the art such as from about 0.01, 0.05, or even 0.08% to about 0.5, 0.4, or even 0.3% by weight of the total polymerization reaction mixture. Typical cross-linkers comprise at least two polymerizable double bonds, and include tripropylene glycol diacrylate, ethylene glycol dimethacrylate, triacrylate, polyethylene glycol diacrylate (polyethylene glycol (PEG) molecular weight between about 100 and about 4000, for example PEG400 or PEG600), and methylene bis acrylamide. In one embodiment, the composition is substantially free (i.e., less than 0.001, or even 0.01 wt %) of conventional cross-linking agents as in known in the art and disclosed, for example, in Haraguchi et al. in Macromolecules v. 36 (2003) p. 5732-5741.

The hydrophilic monomers in the present invention are preferably interactive with the water-swellable clay, when polymerized. Preferably, some of the hydrophilic monomers have functional groups which can form hydrogen bonds, ionic bonds, and coordinate bonds, and covalent bonds with the water-swellable clay. Examples of such functional groups include an amide group, an amino group, a hydroxy group, a tetramethyl ammonium group, a silanol group, and an epoxy group.

Clay can be added to a hydrogel composition to enhance the mechanical properties in the composites comprising large amounts of water. The water-swellable clay of the present disclosure, is a clay mineral capable of swelling and uniformly dispersing, in water or a mixed solvent of water and an organic solvent. In one embodiment, the water-swellable clay is an inorganic clay mineral capable of uniformly dispersing in a molecular form (single layer) or level close thereto in water. More specifically, the water-swellable clay may contain sodium as an interlayer ion. Exemplary water-swellable clays include: synthetic hectorite $[Na_{0.3}(Mg,Li)_3Si_4O_{10}(OH)_2]$, saponite $[Ca_{0.25}(Mg,Fe)_3((Si,Al)_4O_{10})(OH)_2 \cdot n(H_2O)]$, montmorillonite $[(Na,Ca)_{0.33}(Al,Mg)_2(Si_4O_{10})(OH)_2 \cdot nH_2O]$, laponite $[Na^{+0.7}[(Si_3Mg_{5.5}Li_{0.3})O_{20}(OH)_4]^{-0.7}]$, monitrite, and synthetic mica.

The aqueous compositions of the present disclosure can comprise at least 0.1% wt of the water-swellable clay versus the total weight of the aqueous composition. In one embodiment, the amount of water-swellable clay in the aqueous composition is at least 0.3, 0.5, or even 1 wt %; and at most 10, 15, or even 20 wt % versus the total weight of the aqueous composition.

The aqueous compositions of the present disclosure can comprise at least one of a type I or type II photoinitiator.

The aqueous composition of the present disclosure can in some embodiments comprise at least two different initiators: a first initiator, which is a Type I photoinitiator; and a second initiator, which is a Type II photoinitiator.

Photoinitiators for radical polymerization are classified in the art as cleavage (Type I) and hydrogen-abstraction (Type II) initiators. A Type I initiator, upon absorption of light, spontaneously undergoes "α-cleavage", yielding the initiating radical immediately. A Type II initiator is a photoinitiator which, when activated by actinic radiation, forms free radicals by hydrogen abstraction from a second (H-donor) compound to generate the actual initiating free radical. This second compound is called a polymerization synergist or co-initiator.

Type I and Type II photoinitiators are known in the art. These photoinitiators may not however, have sufficient water solubility to be used in the aqueous hydrogel compositions of the present disclosure. To improve the solubility of the photoinitiator, as is known in the art, the photoinitiator can be derivatized with a (more) hydrophilic group, the counter ion can be adjusted to improve the compound's water solubility, and/or a co-solvent can be used to aid the dissolution of the photoinitiator in the aqueous composition.

Examples of Type I photoinitiators are benzoin derivatives, methylolbenzoin and 4-benzoyl-1,3-dioxolane derivatives, benzilketals, α,α-dialkoxyacetophenones, α-hydroxy alkylphenones, α-aminoalkylphenones, acylphosphine oxides, bisacylphosphine oxides, acylphosphine sulphides, halogenated acetophenone derivatives, and the like. Exemplary water-soluble Type I photoinitiators include: 4-[2-(4-morpholino)benzoyl-2-dimethylamino]-butylbenzene-sulfonate salt, and phenyl-2,4,6-trimethyl-benzoylphosphinate salt. Suitable salts include, for example, sodium and lithium cations. A commercial example of suitable water-soluble Type I photoinitiator is available from BASF SE, Ludwigshafen, Germany, under the trade designation: "IRGACURE 2959" (2-hydroxy-4'-(2-hydroxyethoxy)-2-methyl propiophenone).

Examples of Type II photoinitiators are modified benzophenones, benzils, and thioxanthones.

Exemplary water-soluble Type II photoinitiators include: 4-(3-sulfopropyloxy)benzophenone and 2-(3-sulfopropyloxy) thioxanthene-9-one, and 2-, 3-, and 4-carboxybenzophenone.

In the present disclosure, the at least one Type I and the at least one Type II photoinitiators are both water-soluble, which means that at ambient conditions (e.g., 23° C.), the photoinitiator has a solubility of at least 0.01, 0.1, 0.25, 0.5, 1, 2, 5 or even 8% by weight in water. If the solubility of the photoinitiator in water is too low, the photoinitiator will not be available for radical generation.

In one embodiment, the aqueous composition comprises at least 0.01, 0.05, 0.1, or even 0.5 wt %; and at most 1, 2, 4, or even 5 wt % of the first initiator, Type I based on the total weight of the aqueous composition.

In one embodiment, the aqueous composition comprises at least 0.01, 0.05, 0.1, 0.2, or even 0.5 wt %; and at most 1, 2, 4, or even 5 wt % of the second initiator, Type II based on the total weight of the aqueous composition.

Typically the weight ratio Type I photoinitiator:Type II photoinitiator is between 10:1 and 1:10, preferably between 5:1 and 1:5.

In one embodiment, the addition of clay, monomers (or impurities therein), and/or additives (or impurities therein) employed can increase the pH of the aqueous composition. The aqueous composition can comprise at least 0.1% water-swellable clay.

Such additional ingredients are selected from additives known in the art, including, for example, water, organic plasticizers, surfactants, humectant, preservative, particles, polymeric material (hydrophobic or hydrophilic in nature, including proteins, enzymes, naturally occurring polymers and gums), synthetic polymers with and without pendant carboxylic acids, electrolytes, osmolytes, pH regulators, colorants, chloride sources, bioactive compounds and mixtures thereof. In some embodiments, the additional ingredients may serve more than one purpose. For example, glycerol may serve as an organic plasticizer and an osmolyte.

Exemplary humectant can include glycerol, sorbitol, xylitol, maltitol, polyethylene glycol, propylene glycol, butylene glycol, and urea. Exemplary preservative can include germaben II, methylparaben, propylparaben, butylparaben, isothiazolinones, phenoxyethanol, or organic acid such as benzoic acid, sorbic acid, levulinic acid, and anisic acid. Exemplary particles can include those particles with at least one dimension less than 100 nm, such as silica, zirconia, gold, and silver nanoparticles as well as natural and synthetic clays.

The adhesive layer can include a viscoelastic or elastomeric adhesive. Viscoelastic or elastomeric adhesives can include those described in U.S. Pat. App. Pub. No. 2016/0016338 (Radcliffe et al.), for example, pressure-sensitive adhesives (PSAs), rubber-based adhesives (e.g., rubber, urethane) and silicone-based adhesives. Viscoelastic or elastomeric adhesives also include heat-activated adhesives which are non-tacky at room temperature but become temporarily tacky and are capable of bonding to a substrate at elevated temperatures. Heat activated adhesives are activated at an activation temperature and above this temperature have similar viscoelastic characteristics as PSAs. Viscoelastic or elastomeric adhesives may be substantially transparent and optically clear. Any of the viscoelastic or elastomeric adhesives of the present description may be viscoelastic optically clear adhesives. Elastomeric materials may have an elongation at break of greater than about 20 percent, or greater than about 50 percent, or greater than about 100 percent. Viscoelastic or elastomeric adhesive layers may be applied directly as a substantially 100 percent solids adhesive or may be formed by coating a solvent-borne adhesive and evaporating the solvent. Viscoelastic or elastomeric adhesives may be hot melt adhesives which may be melted, applied in the melted form and then cooled to form a viscoelastic or elastomeric adhesive layer. Suitable viscoelastic or elastomeric adhesives include elastomeric polyurethane or silicone adhesives and the viscoelastic optically clear adhesives CEF22, 817x, and 818x, all available from 3M Company, St. Paul, Minn. Other useful viscoelastic or elastomeric adhesives include PSAs based on styrene block copolymers, (meth)acrylic block copolymers, polyvinyl ethers, polyolefins, and poly(meth)acrylates. Adhesive layer can include a UV cured adhesive.

In some embodiments (for example as shown in FIGS. 1A-1B, and 2A-2B), the hydrogel can be formed by curing the aqueous composition after the aqueous composition is placed into the apertures.

The near field communication device used in the current disclosure can include those described in WO 2016/160359 A1 (Jesme et al.). It is sometimes desired to attach electronics to human skin. Such electronics includes radio-frequency identification (RFID) or Near Field Communication (NFC) tags that can be used, for example, for sensing, health monitoring, or authentication applications. For example, a person could attach an NFC tag to their skin which could then automatically provide the desired authentication via NFC to an NFC-enabled computer, tablet, phone, or the like that the person may use. A near field communication device may be configured to operate according to Near Field Communication standards as defined by the NFC Forum <https://nfc-forum.org/>, or other suitable standards include ISO/IEC 18092, ECMA-340, or ECMA-352, ISO/IEC 15693, ISO/IEC 14443, ISO/IEC 18000-3, for example. A near field communication device may be configured to operate in the electromagnetic near-field based on its analog properties such as resonance frequency or quality factor.

In some embodiments, the near field communication device can include a memory with a cryptographic key. In some embodiments, the near field communication device can have a memory with a unique identification (ID). The near field communication device may have a memory with lockable usage information. The near field communication device can have an antenna having a single loop. Antenna includes electrically conductive trace forming a single loop. It has been found that near field communication devices having only one loop or having only a few loops can provide improved and more consistent performance when disposed on or near skin or on or near other fluid-containing medium with varying level of hydration such as a hydrogel.

In some embodiments, the near field communication device includes a capacitor electrically in parallel with an antenna and an integrated circuit. The near field communication device can have capability to sense the hydration level of the hydrogel. The near field communication device can include a compliant segmented conductive shielding layer between its antenna and the hydrogel. The near field communication device can include a low-dielectric coating or spacing layer between its antenna and the hydrogel. near field communication device can have one or more distinct non-adhesive regions as attachments to isolate stress from higher modulus portions of the near field communication device.

The near field communication device can have conductors described in WO 2016/109168 A3 (Gabriel et al.). The conductors can be elongated conductors centered on an axis along a length of the conductor such that the axis has a continuous first derivative with respect to a reference line, the reference line being parallel to an elongation direction of the conductor, and the first derivative is zero at a plurality of spaced apart first locations, In some embodiments, the axis has a second derivative with respect to the reference line discontinuous at at least one second location, and the conductor at each first location is wider than at each second location. In some other embodiments, the axis has a second derivative with respect to the reference line that is substantially zero at at least one second location, and the conductor at each first location is wider than at each second location. In some embodiments the at least one second location includes at least two second locations.

In some embodiments, the conductors can be centered on an axis along a length of the conductor and defining a plane of the conductor, the conductor having a width along a direction parallel to the plane of the conductor. The axis has a continuous radius of curvature and at a plurality of spaced apart first locations the axis has a local minimum radius of curvature and the conductor has a local maximum width. In some embodiments, the local maximum width at each first location is greater than the width of the conductor at any other location that is not a first location. In some embodiments, a magnitude of a second derivative of the axis with respect to a reference line the reference line being parallel to an elongation direction of the conductor, is continuous along the length of the conductor.

In some embodiments, the conductors can be electrically continuous conductor elongated along a length of the conductor, the conductor having a substantially constant height, a varying width, and a varying radius of curvature along the length of the conductor. Along the length of the conductor, a greater radius of curvature of the conductor corresponds to a smaller width of the conductor and a smaller radius of curvature of the conductor corresponds to a greater width of the conductor. In some embodiments, along the length of the conductor, locations of substantially equal radii of curvature correspond to substantially equal widths.

In some embodiments, the conductors can be an electrically continuous conductor elongated along a length of the conductor, the conductor having a varying width and a varying radius of curvature along the length of the conductor. Along the length of the conductor, the width of the conductor increases with decreasing radius of curvature of the conductor, and the width of the conductor decreases with increasing radius of curvature of the conductor.

In some embodiments, the conductors can be an elongated conductor centered on an axis along a length of the conductor. At each of a plurality of spaced apart first location on the axis, a line tangent to the axis at the first location is parallel to an elongation direction of the conductor, and at each of the plurality of spaced apart second locations on the axis, a line tangent to the axis at the second location not being parallel to the reference line. The conductor is wider at each first location and narrower at each second location.

In some embodiments, the conductors can be an electrically continuous conductor elongated along a length of the conductor, the conductor having a varying thickness and a varying radius of curvature along the length of the conductor. Along the length of the conductor, a greater radius of curvature of the conductor corresponds to a smaller thickness of the conductor and a smaller radius of curvature of the conductor corresponds to a greater thickness of the conductor. In some embodiments, the conductor has a varying width along the length of the conductor, such that along the length of the conductor, a greater radius of curvature of the conductor corresponds to a smaller width of the conductor and a smaller radius of curvature of the conductor corresponds to a greater width of the conductor.

In some embodiments, the near field communication device can be in contact with the hydrogel. In some embodiments, the near field communication device can be attached to the hydrogel. In some embodiments, the aperture can have a cross section in the shape of a circle, oval, ellipse, or polygon (such as a 3-12 sided polygon). Some typical polygon shapes include square, rectangle, pentagon, hexagon, heptagon, and octagon shapes. In some embodiments, the near field communication device has aperture. In some embodiments, the near field communication device aperture can be in the shape of a circle, oval, ellipse, or polygon (such as a 3-12 sided polygon). Some typical polygon shapes include square, rectangle, pentagon, hexagon, heptagon, and octagon shapes. In some embodiments, the polymeric substrate and the near field communication device aperture have the same shape.

In some embodiments, the polymeric substrate aperture and the near field communication device aperture have the same diameter. In some embodiments the polymeric substrate aperture has a diameter of about 1 mm to 100 mm. In some embodiments the polymeric substrate aperture has a diameter of about 5 mm to 75 mm. In some embodiments the polymeric substrate aperture has a diameter of about 10 mm to 50 mm.

In some embodiments the near field communication device aperture defines an area of 1 mm$^2$ to 10,000 mm$^2$. In some embodiments the near field communication device aperture defines an area of 25 mm$^2$ to 5,625 mm$^2$. In some embodiments the near field communication device aperture defines an area of 10 mm$^2$ to 2,500 mm$^2$. In some embodiments the near field communication device has a second aperture opposite from the aperture. In some embodiments, the device contains an open channel between the two apertures and at least a portion of the hydrogel is in the channel. In some embodiments, the distance of the channel between the two apertures is about 0.5 mm to 10 mm.

In some embodiments, a system for delivering ultrasonic radiation to a subject is provide. The system can include the ultrasonic coupling device of the current application and an ultrasonic transducer with a probe. The probe of the ultrasonic transducer can be in contact with the hydrogel.

The following embodiments are intended to be illustrative of the present disclosure and not limiting.

EMBODIMENTS

Embodiment 1 is an ultrasonic coupling device comprising a hydrogel wherein the hydrogel has a water content of at least 10 wt %; and a near field communication device.

Embodiment 2 is the ultrasonic coupling device of embodiment 1, wherein the hydrogel is derived from an aqueous composition, the aqueous composition comprising: a hydrophilic monomer capable of free radical polymerization selected from at least one of (meth)acrylate or (meth) acrylamide; and an initiator of free radical polymerization.

Embodiment 3 is the ultrasonic coupling device of embodiment 1, wherein the aqueous has a pH less than 9.5.

Embodiment 4 is the ultrasonic coupling device of any of embodiments 1-3, wherein the aqueous composition further comprises at least one of a type I or type II photoinitiator.

Embodiment 5 is the ultrasonic coupling device of any of embodiments 1-4, wherein the hydrogel further comprises a particle with at least one dimension less than 100 nm.

Embodiment 6 is the ultrasonic coupling device of any of embodiments 1-5, wherein the near field communication device comprises an aperture and the hydrogel at least partially fills in the aperture of the near field communication device.

Embodiment 7 is the ultrasonic coupling device of any of embodiments 1-6, wherein the near field communication device is in contact with the hydrogel.

Embodiment 8 is the ultrasonic coupling device of any of embodiments 1-7, wherein the near field communication device is attached to the hydrogel.

Embodiment 9 is the ultrasonic coupling device of any of embodiments 1-8, wherein the near field communication device comprises a memory with lockable usage information.

Embodiment 10 is the ultrasonic coupling device of any of embodiments 1-9, wherein the near field communication device comprises an antenna having a single loop.

Embodiment 11 is the ultrasonic coupling device of any of embodiments 1-10, wherein the aqueous composition further comprises a humectant selected from glycerol, sorbitol, xylitol, maltitol, polyethylene glycol, propylene glycol, butylene glycol, and urea.

Embodiment 12 is the ultrasonic coupling device of any of embodiments 1-11, wherein the aqueous composition further comprises a preservative selected from the germaben II, methylparaben, propylparaben, butylparaben, isothiazolinones, phenoxyethanol, or organic acid such as benzoic acid, sorbic acid, levulinic acid, and anisic acid.

Embodiment 13 is the ultrasonic coupling device of any of embodiments 1-12, wherein the near field communication device comprises a capacitor electrically in parallel with an antenna and an integrated circuit.

Embodiment 14 is the ultrasonic coupling device of any of embodiments 1-13, the near field communication device comprises a polymeric substrate.

Embodiment 15 is the ultrasonic coupling device of any of embodiments 1-13, further comprising a polymeric substrate having an aperture between the hydrogel and the near field communication device.

Embodiment 16 is the ultrasonic coupling device of embodiment 15, wherein the hydrogel is covalently bonded to the polymeric substrate.

Embodiment 17 is the ultrasonic coupling device of embodiment 15, further comprising an adhesive layer between the near field communication device and the polymeric substrate.

Embodiment 18 is the ultrasonic coupling device of embodiment 15, wherein the polymeric substrate comprises at least one of polyurethanes, polyamide, polyester, and polypropylene.

Embodiment 19 is the ultrasonic coupling device of embodiment 15, further comprising a second polymeric substrate having an aperture and the hydrogel is covalently bonded to the second polymeric substrate.

Embodiment 20 is the ultrasonic coupling device of any of the embodiments 1-19, wherein the near field communication device has aperture.

Embodiment 21 is the ultrasonic coupling device of embodiment 20, wherein the near field communication device has a second aperture opposite from the aperture.

Embodiment 22 is the ultrasonic coupling device of embodiment 21, wherein the device contains an open channel between the two apertures of the near field communication device and at least a portion of the hydrogel is in the channel.

Embodiment 23 is a system for delivering ultrasonic radiation to a subject comprising the ultrasonic coupling device of any of the embodiments 1-22 and an ultrasonic transducer with a probe, wherein the probe of the ultrasonic transducer is in contact with the hydrogel.

The following working examples are intended to be illustrative of the present disclosure and not limiting.

EXAMPLES

Materials

| REAGENT | SOURCE |
| --- | --- |
| N,N-dimethylacrylamide (DMA) | Sigma-Aldrich Corporation, St. Louis, MO |
| Methylenebisacrylamide (MBA) | Sigma-Aldrich Corporation, St. Louis, MO |
| IRGACURE 2959 (1-[4-(2-hydroxyethoxy)phenyl]-2-hydroxy-2-methyl-1-propane-1-one) | BASF Corporation, Florham Park, NJ |
| LAPONITE XLG Clay | Southern Clay Products, Gonzales, TX |
| Citric acid | Alfa Aesar, Ward Hill, MA |
| Benzophenone | Alfa Aesar, Ward Hill, MA |

Unless otherwise noted, all aqueous compositions were prepared with 18 MΩ water from a water purification system (available under the trade designation "Milli-Q" from EMD Millipore, Billerica, MA).

An Orion 3 STAR pH Meter equipped with an 8157 BNC Ross Ultra pH/ATC Triode electrode (Thermo Scientific, Waltham, MA) was used to measure pH. The pH meter was calibrated using a three point calibration that followed the vendor provided procedure with calibration standards at pH 4, 7, and 10 (BDH, Dubai, UAE).

Preparation of Aqueous Composition

A glass jar (0.95 L) was equipped with an overhead stirrer (VOS PC Overhead Stirrer, obtained from VWR International, Radnor, PA) that had a 60 cm half-moon shaped impeller. The jar was charged with water (522 mL) and the overhead stirrer was set at 400 rpm. LAPONITE XLG clay (18 g) was slowly added and the mixture was stirred for 30 minutes. The resulting clear solution was charged with a solution that contained IRGACURE 2959 (300 mg) dissolved in N,N-dimethylacrylamide (62.4 mL). An aqueous solution of methylenebisacrylamide (3 mL, 2% by weight) was added next and the reaction was stirred for 30 minutes. An aqueous solution of citric acid (6 mL, 10% by weight) was then added and the reaction was stirred for 5 minutes. The mixing was stopped and the resulting aqueous composition was maintained for 15-60 minutes in order to build the viscosity of the formulation. The pH of the aqueous composition was measured as 7.0.

Example 1. Ultrasonic Coupling Device

A sheet of translucent polyurethane film (20 microns thick) with a white paper carrier backing (130 microns thick) on one side (obtained from the 3M Corporation, St. Paul, MN under the designation "3M 9832F Film on White Paper Carrier") was laminated to a double-sided tape (obtained from the 3M Corporation under the designation "3M 1509 Medical Tape") on the exposed polyurethane surface of the film. The white paper was removed exposing the opposite polyurethane surface. The newly exposed polyurethane film surface was coated with a 1% by weight solution of benzophenone in hexane using a #14 mayer rod. The coating was dried at ambient conditions. A 19 mm hole was cut out of the laminate using a circular die. The paper release was then removed from the double-sided tape and the newly exposed adhesive was laminated to a clear PET release liner coated with a silicone release coating (51 microns thick, obtained from Dupont Teijin Films, Dupont Company, Wilmington, DE) such that the release coating was in contact with the adhesive. A square section (approximately 12.7 cm by 12.7 cm) was cut from the laminate with the 19 mm aperture positioned in the center of the square. Approximately 20 mL of the aqueous composition described above was then applied to the polyurethane surface of the laminate. A clear PET release liner coated with a silicone release coating (51 microns thick, obtained from Dupont Teijin Films) was applied to the top of the aqueous composition (with the release surface facing the aqueous composition). The aqueous composition spread across the polyurethane surface filling the aperture. The construction was shimmed to a thickness of 3.2 mm using pressure. Ultraviolet (UV) light initiated grafting was conducted by irradiating the coated sheet for 20 minutes using a UV light stand (Classic Manufacturing, Inc., Oakdale, MN). The stand was equipped with sixteen 40 watt, 350 nm black light tubes [Sylvania RG2 F40/350BL/ECO tubes (117 cm long)] with 8 light tubes positioned in a row above the sheet and 8 tubes positioned in a row below the sheet. The light tubes in each row were spaced 5.1 cm on center and positioned 3.8 cm from the surface of the sheet. Following the curing procedure, the two PET release liners were removed. A 38 mm circle was die cut out of the hydrogel-polyurethane film laminate with the hydrogel filled aperture of the polyurethane film positioned directly in the center. A 19 mm aperture was die cut in the center (plastic substrate portion) of a Smartrac BULLSEYE NFC tag (#3002646, Smartrac Company, Amsterdam, Netherlands). The tag was aligned with the outer diameter of the film component with the adhesive surface of the tag adhered to adhesive surface on the polyurethane film.

Example 2. Ultrasonic Coupling Device

A 19 mm aperture was die cut through the center (plastic substrate portion) of a 1624 W TEGADERM Film Adhesive Bandage (obtained from the 3M Corporation). The adhesive surface of the bandage was attached the surface of the NFC tag of Example 1 so that the aperture of the bandage was aligned with the aperture of the tag.

Example 3 Ultrasonic Coupling Device

A sheet of translucent polyurethane film (20 microns thick) with a white paper carrier backing (130 microns thick) on one side (obtained from the 3M Corporation, St. Paul, MN under the designation "3M 9832F Film on White Paper Carrier") was laminated to a double-sided tape (obtained from the 3M Corporation under the designation "3M 1509 Medical Tape") on the exposed polyurethane surface of the film. The white paper was removed exposing the opposite polyurethane surface. The newly exposed polyurethane film surface was coated with a 1% by weight solution of benzophenone in hexane using a #14 mayer rod. The coating was dried at ambient conditions. A circular die was used to cut two 19 mm holes in the coated film spaced at a distance of 10.16 cm on center. The paper release was then removed from the double-sided tape and the exposed adhesive was laminated to a clear PET release liner coated with a silicone release coating (51 microns thick, obtained from Dupont Teijin Films) such that the release coating was in contact with the adhesive. Two square sections (approximately 7.26 cm by 7.26 cm) were cut from the laminate with each section having a 19 mm aperture positioned in the center. Approximately 20 mL of the aqueous composition described above was then applied to the polyurethane surface of one of the square sections. The second square polyurethane film with aperture was positioned over the aqueous composition on the first square section with the polyurethane surface facing the aqueous composition and the edges of the square sections and center apertures aligned. The aqueous composition spread across the polyurethane surfaces filling the apertures. The construction was shimmed to a thickness of 3.2 mm using pressure. Ultraviolet (UV) light initiated grafting was conducted by irradiating the coated sheets for 20 minutes using a UV light stand (Classic Manufacturing, Inc., Oakdale, MN). The stand was equipped with sixteen 40 watt, 350 nm black light tubes [Sylvania RG2 F40/350BL/ECO tubes (117 cm long)] with 8 light tubes positioned in a row above the sheet and 8 tubes positioned in a row below the sheet. The light tubes in each row were spaced 5.1 cm on center and positioned 3.8 cm from the surface of the sheet. Following the curing procedure, the two PET release liners were removed. A 38 mm circle was die cut out of the polyurethane film-hydrogel-polyurethane film laminate so that the hydrogel filled apertures of the polyurethane films were positioned in the center of the circle. A 19 mm aperture was die cut in the center (plastic substrate portion) of a Smartrac BULLSEYE NFC tag (#3002646, Smartrac Company). The tag was aligned with the outer diameter of one of the polyurethane film layers and the adhesive surface of the tag was adhered to the adhesive surface on the polyurethane film.

Example 4. Ultrasonic Coupling Device

A 19 mm aperture was die cut through the center of a 1624 W TEGADERM Film Adhesive Bandage (obtained from the 3M Corporation). The adhesive coated polyurethane surface of the Device of Example 3 (i.e. the surface located opposite from the tag attached surface) was attached to the non-adhesive surface of the bandage so that the hydrogel filled aperture of the polyurethane film was aligned with the aperture of the bandage.

All references and publications cited herein are expressly incorporated herein by reference in their entirety into this disclosure. Illustrative embodiments of this invention are discussed and reference has been made to possible variations within the scope of this invention. For example, features depicted in connection with one illustrative embodiment may be used in connection with other embodiments of the invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

What is claimed is:

1. An ultrasonic coupling device comprising
  a hydrogel wherein the hydrogel has a water content of at least 10 wt %; and
  a near field communication device;
  wherein the near field communication device comprises a polymeric substrate.

2. The ultrasonic coupling device of claim 1, wherein the hydrogel is derived from an aqueous composition, the aqueous composition comprising:
  a hydrophilic monomer capable of free radical polymerization selected from at least one of (meth)acrylate or (meth)acrylamide; and
  an initiator of free radical polymerization.

3. The ultrasonic coupling device of claim 2, wherein the aqueous composition has a pH less than 9.5.

4. The ultrasonic coupling device of claim 2, wherein the aqueous composition further comprises at least one of a type I or type II photoinitiator.

5. The ultrasonic coupling device of claim 1, wherein the hydrogel further comprises a particle with at least one dimension less than 100 nm.

6. The ultrasonic coupling device of claim 1, wherein the near field communication device comprises an aperture and the hydrogel at least partially fills in the aperture of the near field communication device.

7. The ultrasonic coupling device of claim 1, wherein the near field communication device is in contact with the hydrogel.

8. The ultrasonic coupling device of claim 1, wherein the near field communication device is attached to the hydrogel.

9. The ultrasonic coupling device of claim 1, wherein the near field communication device comprises an antenna having a single loop.

10. The ultrasonic coupling device of claim 2, wherein the aqueous composition further comprises a humectant selected from glycerol, sorbitol, xylitol, maltitol, polyethylene glycol, propylene glycol, butylene glycol, and urea.

11. The ultrasonic coupling device of claim 2, wherein the aqueous composition further comprises a preservative selected from the germaben II, methylparaben, propylparaben, butylparaben, isothiazolinones, phenoxyethanol, or organic acid such as benzoic acid, sorbic acid, levulinic acid, and anisic acid.

12. The ultrasonic coupling device of claim 1, wherein the near field communication device comprises a capacitor electrically in parallel with an antenna and an integrated circuit.

13. The ultrasonic coupling device of claim 1, further comprising a polymeric substrate having an aperture between the hydrogel and the near field communication device.

14. The ultrasonic coupling device of claim 13, wherein the hydrogel is covalently bonded to the polymeric substrate.

15. The ultrasonic coupling device of claim 13, further comprising an adhesive layer between the near field communication device and the polymeric substrate.

16. The ultrasonic coupling device of claim 13, wherein the polymeric substrate comprises at least one of polyurethanes, polyamide, polyester, and polypropylene.

17. The ultrasonic coupling device of claim 13, further comprising a second polymeric substrate having an aperture and the hydrogel is covalently bonded to the second polymeric substrate.

18. A system for delivering ultrasonic radiation to a subject comprising the ultrasonic coupling device of claim 1 and an ultrasonic transducer with a probe, wherein the probe of the ultrasonic transducer is in contact with the hydrogel.

19. An ultrasonic coupling device comprising
a hydrogel wherein the hydrogel has a water content of at least 10 wt %; and
a near field communication device;
wherein the near field communication device comprises a memory with lockable usage information.

\* \* \* \* \*